(12) United States Patent
Mahmud et al.

(10) Patent No.: US 9,242,123 B2
(45) Date of Patent: Jan. 26, 2016

(54) HAIR THICKENING COMPOSITIONS AND METHODS OF USE

(71) Applicant: The Procter & Gamble Company, Cincinnati, OH (US)

(72) Inventors: Goher Mahmud, Mason, OH (US); Mary Jane Combs, Covington, KY (US); Kelly Rose Kroger Lyons, Blanchester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/275,252

(22) Filed: May 12, 2014

(65) Prior Publication Data

US 2014/0341834 A1  Nov. 20, 2014

Related U.S. Application Data

(60) Provisional application No. 61/824,207, filed on May 16, 2013.

(51) Int. Cl.

| | |
|---|---|
| *A61K 8/73* | (2006.01) |
| *A61Q 5/00* | (2006.01) |
| *A61K 8/34* | (2006.01) |
| *A61K 8/49* | (2006.01) |
| *A61K 8/42* | (2006.01) |
| *A61Q 5/12* | (2006.01) |
| *A61K 8/67* | (2006.01) |
| *A61K 8/81* | (2006.01) |
| *A61Q 7/00* | (2006.01) |

(52) U.S. Cl.
CPC . *A61Q 5/00* (2013.01); *A61K 8/345* (2013.01); *A61K 8/347* (2013.01); *A61K 8/42* (2013.01); *A61K 8/4953* (2013.01); *A61K 8/675* (2013.01); *A61K 8/8158* (2013.01); *A61Q 5/12* (2013.01); *A61Q 7/00* (2013.01)

(58) Field of Classification Search
CPC ....... A61K 8/345; A61K 8/4953; A61K 8/42; A61K 8/347; A61K 8/675; A61K 8/8158; A61Q 5/00; A61Q 7/00; A61Q 5/12
See application file for complete search history.

(56) References Cited

U.S. PATENT DOCUMENTS

| | | | |
|---|---|---|---|
| 4,324,553 A * | 4/1982 | Bugaut et al. | 8/407 |
| 6,858,216 B2 * | 2/2005 | Schulze zur Wiesche et al. | 424/401 |
| D681,876 S | 5/2013 | Still | |
| 2002/0114770 A1 * | 8/2002 | Bradley et al. | 424/62 |
| 2005/0100525 A1 * | 5/2005 | Taguchi et al. | 424/74 |
| 2008/0059313 A1 | 3/2008 | Oblong | |
| 2009/0264449 A1 | 10/2009 | Iwata | |
| 2013/0164390 A1 | 6/2013 | Richards | |
| 2013/0284195 A1 | 10/2013 | Murdock | |
| 2013/0284196 A1 | 10/2013 | Murdock | |
| 2014/0093466 A1 | 4/2014 | Combs | |

FOREIGN PATENT DOCUMENTS

| | | | | |
|---|---|---|---|---|
| EP | 1430933 A2 | 6/2004 | | |
| WO | WO 2009107074 A1 * | 9/2009 | | A61K 8/42 |
| WO | WO2011156311 A2 | 12/2011 | | |
| WO | WO2012038334 A1 | 3/2012 | | |

\* cited by examiner

*Primary Examiner* — Lezah Roberts
*Assistant Examiner* — Nannette Holloman
(74) *Attorney, Agent, or Firm* — James T. Fondriest

(57) ABSTRACT

Provided is a method for increasing hair shaft diameter, the method including applying a hair care composition to a region of the hair, wherein the hair care composition includes from about 0.05% to about 0.5% resorcinol and from about 1% to about 1.7% of a rheology modifier.

12 Claims, No Drawings

HAIR THICKENING COMPOSITIONS AND METHODS OF USE

FIELD OF THE INVENTION

The present invention relates to hair care compositions comprising one or more actives useful for increasing hair diameter and methods of use thereof.

BACKGROUND OF THE INVENTION

Many attributes contribute to the appearance of hair considered to be attractive. For instance, hair with a full and thick appearance is very desirable. In contrast, hair with a thin appearance is not as attractive, and can even lead to a perception that the thin-haired individual is older than their chronological age. Because of the foregoing problems associated with thin hair, many individuals expend great effort and time on grooming, yet still do not attain their desired hairstyle and appearance. This can lead to frustration and/or lack of confidence in his or her appearance. These problems can be experienced by both female and male consumers and at a variety of ages.

In view thereof, there is a need to provide consumers with a hair care composition that includes actives which increase hair diameter and therefore create a fuller and thicker appearance of the hair.

SUMMARY OF THE INVENTION

Provided is a method for increasing hair shaft diameter, the method including applying a hair care composition to a region of the hair, wherein the hair care composition includes from about 0.05% to about 0.5% resorcinol and from about 1% to about 1.7% of a rheology modifier.

Also provided is a hair care composition comprising from about 0.05% to about 0.5% resorcinol and from about 1% to about 1.7% of a rheology modifier.

These and other features, aspects, and advantages of the present invention will become evident to those skilled in the art from a reading of the present disclosure.

DETAILED DESCRIPTION OF EMBODIMENTS OF THE INVENTION

While the specification concludes with the claims particularly pointing and distinctly claiming the invention, it is believed that embodiments of the present invention will be better understood from the following description. In all embodiments of the present invention, all weight percentages are by weight of the total composition, unless specifically stated otherwise. All ratios are weight ratios, unless specifically stated otherwise. All ranges are inclusive and combinable. The number of significant digits conveys neither limitations on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

As used herein, the term "hair care compositions" are compositions that are applied to the hair and/or the skin underneath the hair, including compositions used to treat or care for the hair. Products contemplated by the phrase "hair care composition" include, but are not limited to after-shave tonics and lotions, creams, emulsions, foams, hair conditioners (rinse-off and leave-on), hair colorants, hair tonics, liquids, lotions, mousses, propellant lotions, shampoos, shave gels, temporary beard hair dyes, and the like.

"Mammalian hair," as referenced herein, includes hair on any part of the body of a mammal, and can include but is not limited to facial, cranial, or body hair. For instance, it can include hair on the scalp, head, neck, beard, moustache, eyebrows and sideburns hair.

I. Hair Care Compositions

According to an embodiment of the invention, the hair care composition may include one or more solvents, such as dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, and 1,6-hexanediol, or combinations thereof.

According to yet another embodiment, the hair care composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

A. Indole Compounds

The hair care compositions can further include an indole compound. As used herein, "indole compound" means one or more indoles, derivatives thereof, mixtures thereof, or salts thereof. Accordingly, the composition may include from about 0.1% to about 10% of the indole compound, from about 0.5% to about 5% of the indole compound, or from about 1% to about 2% of the indole compound, for example, wherein the percentage is a weight percentage based on the total weight of the final hair care composition.

B. Xanthine Compounds

The hair care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1% to about 10% of the xanthine compound, from about 0.5% to about 5% of the xanthine compound, or from about 1% to about 2% of the xanthine compound, for example, wherein the percentage is a weight percentage based on the total weight of the final hair care composition. For example, the hair care composition may further include about 0.75% of caffeine.

In an embodiment, the amount of xanthine may be decreased to lessen potential white residue the may result from various formulations when the xanthine is present in higher amounts. In an embodiment, the hair care composition may comprise from about 0.01% to about 1% xanthine, alternative from about 0.01% to about 0.75% xanthine, alternatively from about 0.01% to about 0.5% xanthine, alternatively from about 0.01% to about 0.25% xanthine, and alternatively from about 0.01% to about 0.1% xanthine. In an embodiment, the hair care composition may have no xanthine.

C. Vitamin $B_3$ Compounds

The hair care compositions can further include a vitamin B3 compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. Accordingly, the composition may include from about 0.1% to about 25% of the vitamin $B_3$ compound; from about 0.5% to about 15% of the vitamin $B_3$ compound; or from about 3.5% to about 7.5% of the vitamin $B_3$ compound, for example, wherein the percentage is a weight percentage based on the total weight of the final hair care composition. For example, the hair care composition may further include about 2.5% of vitamin $B_3$.

D. Panthenol Compounds

The hair care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, the composition may include from about 0.01% to about 5% of the panthenol compound; from about 0.03% to about 3% of the panthenol compound; from about 0.05% to about 2% of the panthenol compound; or from about 0.1% to about 1% of the panthenol compound, for example, wherein the percentage is a weight percentage based on the total weight of the final hair care composition. For example, the hair care composition may further include about 0.15% of panthenol.

According to another aspect of the present invention, the hair care compositions may be free of oleanolic acid and/or biotinyl-GHK, which is contrary to that described in U.S. Patent Application No. 20060067905.

E. Hops

In an embodiment, the hair care composition may comprise hops. The hair care composition may comprise from about 0.01% about 5% hops, alternatively from about 0.01% to about 3% hops, alternatively from about 0.01% to about 1.5% hops, and alternatively from about 0.01% to about 1% hops. In an embodiment, the hair care composition may comprise no hops.

The hops may be extracted by different methods, including extraction in glycerin, extraction in water and denatured alcohol, or extraction in propylene glycol. In an embodiment, the hops is extracted in glycerin. In an embodiment, the hops extracted in glycerin may provide improved thickening as compared to other extraction methods. In an embodiment, the hops is of the *Humulus Lupulus* species.

F. Resorcinol

In an embodiment, the hair care composition may comprise resorcinol. The hair care composition may comprise from about 1% to about 14% resorcinol, alternatively from about 1% to about 13% resorcinol, alternatively from about 1% to about 11% resorcinol, alternatively from about 1% to about 9% resorcinol, alternatively from about 1% to about 8% resorcinol, alternatively from about 1% to about 4% resorcinol, and alternatively from about 1% to about 3% resorcinol.

In an embodiment, the resorcinol may be chlorinated. In an embodiment, the resorcinol may be non-chlorinated. In an embodiment, the chlorinated resorcinol may provide improved thickening as compared to non-chlorinated resorcinol.

G. Rheology Modifier

In one embodiment, the composition comprises a rheology modifier to increase the substantivity of the composition. Any suitable rheology modifier can be used. In an embodiment, the hair care composition may comprise from about 0.1% to about 10% of a rheology modifier, alternatively from about 0.5% to about 2.2% of a rheology modifier, alternatively from about 0.7% to about 2% of a rheology modifier, alternatively from about 1% to about 1.7% of a rheology, and alternatively from about 1% to about 1.5% of a rheology modifier. In an embodiment, the rheology modifier may be a polyacrylamide thickener.

Non-limiting examples of rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (ME-HEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/ polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and combinations thereof.

H. Carrier

According to another aspect of the present invention, the hair care compositions may further include at least about 20 weight percent of an aqueous carrier. According to one embodiment, the aqueous carrier may be prepared from demineralized or distilled water, for example. Other acceptable carriers that may be used in the aqueous carrier include, but are not limited to alcohol compounds, such as ethanol. According to one embodiment, the composition comprises alcohol, dipropylene glycol, and/or water.

The hair care compositions may have a pH ranging from about 3.0 to about 10, which may be measured by taking a direct pH measurement using a standard hydrogen electrode of the composition at 25° C. Accordingly, the pH of the hair care composition may be within the range from about 6 to about 9, for example.

I. Optional Ingredients

The compositions of the present invention can also additionally comprise any suitable optional ingredients as desired. For example, the composition can optionally include other active or inactive ingredients.

The compositions may include other common hair ingredients such as pyrithione zinc, minoxidil, silicones, glycerin, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

In one embodiment, the composition comprises a rheology modifier to increase the substantivity of the composition, such that it does not drip undesirably onto other areas of the body, onto clothing, or onto home furnishings and may also perform as a film former. Any suitable rheology modifier can be used, for example, a cellulose-based rheology modifier, such as hydroxypropylmethylcellulose. Other non-limiting examples of rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and combinations thereof.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, rinse-off hair products such as conditioners, shampoos, and treatment products; and any other form that may be applied to the hair and preferably applied to the scalp.

II. Method for Increasing Hair Shaft Diameter

The hair care composition described above may also be used in a method for increasing hair shaft diameter. The method may comprise applying the hair care composition to a region of the hair, wherein the hair care composition comprises from about 0.05% to about 0.5% resorcinol and from about 1% to about 1.7% of a rheology modifier.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Example 1

| Component | (wt %) |
|---|---|
| Alcohol 100% DEB 100 (Ethanol) | 50 |
| Sepigel 305 | 1.29 |
| Resorcinol | 0.15 |
| Hops | 0.90 |
| Caffeine | 0.94 |
| Niacinamide | 3.13 |
| Panthenol | 0.19 |
| Fragrance: Watergarden | 0.30 |
| Silicone: Abil B 8832 | 0.30 |
| Deionized water | Qs |

*Sepigel ™ 305: Polyacrylamide/C13-14 Isoparaffin/Laureth-7 from Seppic
*Resorcinol: 1,3-Dihydroxybenzene from Jos H Lowenstein & Sons Inc.
*Hops: *Humulus Lupulus* (Hops) Extract 8060-28-4 from Arch Chemicals, Inc. (extracted in propylene glycol)

Example 2

| Component | (wt %) |
|---|---|
| Alcohol 100% DEB 100 (Ethanol) | 50 |
| Sepigel 305 | 1.89 |
| Resorcinol | 0.15 |
| Hops | 0.90 |
| Caffeine | 0.94 |
| Niacinamide | 3.13 |
| Panthenol | 0.19 |
| Fragrance: Watergarden | 0.30 |
| Silicone: Abil B 8832 | 0.30 |
| Deionized water | Qs |

*Sepigel ™ 305: Polyacrylamide/C13-14 Isoparaffin/Laureth-7 from Seppic
*Resorcinol: 1,3-Dihydroxybenzene from Jos H Lowenstein & Sons Inc.
*Hops: *Humulus Lupulus* (Hops) Extract 8060-28-4 from Arch Chemicals, Inc. (extracted in propylene glycol)

Example 3

| Component | (wt %) |
|---|---|
| Alcohol 100% DEB 100 (Ethanol) | 58 |
| Sepigel 305 | 1.89 |
| Resorcinol | 0.15 |
| Hops | 0.9 |
| Caffeine | 0.95 |
| Niacinamide | 3.15 |
| Panthenol | 0.15 |
| Fragrance: | 0.6 |

-continued

| Component | (wt %) |
|---|---|
| Amaze XT | 0.85 |
| Deionized water | Qs |

*Sepigel ™ 305: Polyacrylamide/C13-14 Isoparaffin/Laureth-7 from Seppic
*Resorcinol: 1,3-Dihydroxybenzene from Jos H Lowenstein & Sons Inc.
*Hops: Humulus Lupulus (Hops) Extract 8060-28-4 from Arch Chemicals, Inc. (extracted in propylene glycol)
*Amaze XT: dehydroxy xanthan gum from Akzo Nobel Data

TABLE 1

| P [%] | N [%] | C [%] | Resorcinol [%] | Hops [%] | Sepigel [%] | Average Thickness Increase [μm] | Viscosity [cps] |
|---|---|---|---|---|---|---|---|
| 0.19 | 3.13 | 0.94 | 0.15 | 0.9 | 0.8 | 9.2 | 300 |
| 0.19 | 3.13 | 0.94 | 0.15 | 0.9 | 1.29 | 11.3 | 2659 |
| 0.19 | 3.13 | 0.94 | 0.15 | 0.9 | 1.89 | 8.1 | 10724 |

*P: Panthenol
*N: Niacinimide
*C: Caffeine
*Sepigel ™ 305: Polyacrylamide/C13-14 Isoparaffin/Laureth-7 from Seppic
*Resorcinol: 1,3-Dihydroxybenzene from Jos H Lowenstein & Sons Inc.
*Hops: Humulus Lupulus (Hops) Extract 8060-28-4 from Arch Chemicals, Inc. (extracted in propylene glycol)

The data in Table 1 surprisingly showed that formulations comprising from about 1% to about 1.7% of a rheology modifier provide a measurable average thickness increase of the hair follicle when compared to higher and lower percentages of rheology modifiers. The Example 1 formula was used to formulate each leg, modifying the levels of the rheology modifier.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care compositions.

Test Methods

Measurement of Average Thickness Increase
1) Asian or Caucasian hair fibers (low-lift general population) are soaked in deionized water for 10 minutes, and allowed to equilibrate overnight in at Controlled Temperature and Humidity room (20 C, 50 RH).
2) The single hair fibers are imaged with microscope and the diameter is measured using software for baseline measurement.
3) The hair fibers are then treated with the hair care composition for 10 minutes to allow for saturation. The fibers are then removed and allowed to equilibrate and dry overnight.
4) The next day, the fibers are imaged and measured for a final reading. For each experiment, untreated control and product treatment controls are ran, and at least 5 fibers are measured per treatment.
5) In order to measure increase in thickness as a function of treatment, the final diameter is subtracted from the initial diameter. The average thickness increase is reported in the Table above, with measurements reported in micrometers.

Viscosity Test Method

The hair care composition may have a viscosity of from about 2,000 cps to about 20,000 cps, alternatively from about 10,000 cps to about 15,000 cps. The viscosity of the hair care composition may be determined by a cone and plate viscometer/rheometer which measures the viscous drag resulting from the sample material contained in the gap between a rotating cone and a stationary plate. The geometry of the cone and plate may be such that the entire sample is subjected to a uniform shear rate. A Brookfield Rheometer RS, with Cone C75-1, 26.7° C. temperature, 2.5 mL sample size, at 2 res/sec for 3 minutes may be used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for increasing hair shaft diameter, the method comprising applying a hair care composition to a region of the hair, wherein the hair care composition comprises:
   a. from about 0.05% to about 0.25% resorcinol;
   b. from about 0.01% to about 1.5% hops;
   c. from about 1% to about 1.7% of a rheology modifier; wherein the rhelolgy modifier is a polyacrylamide thickner; and
   wherein the hair care composition is not a hair dye.

2. The method of claim 1, wherein the hair care composition comprises from about 0.05% to about 0.2% of the resorcinol.

3. The method of claim 1, wherein the hair care composition further comprises from about 0.1% to about 10% caffeine.

4. The method of claim 1, wherein the hair care composition further comprises from about 0.1% to about 25% niacinamide.

5. The method of claim 1, wherein the hair care composition further comprises from about 0.01% to about 3% panthenol.

6. The method of claim 1, wherein the resorcinol is chlorinated.

7. A hair care composition comprising:
   a. from about 0.05% to about 0.25% resorcinol;
   b. from about 0.01% to about 1.5% hops;

c. from about 1% to about 1.7% of a rheology modifier; wherein the rheology modifier is a polyacrylamide thickener; and wherein the hair care composition is not a hair dye.

8. The hair care composition of claim 7, wherein the hair care composition comprises from about 0.05% to about 0.2% of the resorcinol.

9. The hair care composition of claim 7, wherein the hair care composition further comprises from about 0.1% to about 10% caffeine.

10. The hair care composition of claim 7, wherein the hair care composition further comprises from about 0.1% to about 25% niacinamide.

11. The hair care composition of claim 7, wherein the hair care composition further comprises from about 0.01% to about 3% panthenol.

12. The hair care composition of claim 7, wherein the resorcinol is chlorinated.

\* \* \* \* \*